(12) United States Patent
Schorr et al.

(10) Patent No.: US 9,107,656 B2
(45) Date of Patent: Aug. 18, 2015

(54) INTERNAL SUTURING DEVICE LEG SUSPENSION SYSTEM AND METHOD OF USE

(75) Inventors: Gary James Schorr, Apple Valley, MN (US); Jyue Boon Lim, New Brighton, MN (US)

(73) Assignee: ST. JUDE MEDICAL, CARDIOVASCULAR DIVISION, INC., Minnetonka, MN (US)

( * ) Notice: Subject to any disclaimer, the term of this patent is extended or adjusted under 35 U.S.C. 154(b) by 1529 days.

(21) Appl. No.: 11/551,612

(22) Filed: Oct. 20, 2006

(65) Prior Publication Data
US 2008/0097480 A1 Apr. 24, 2008

(51) Int. Cl.
*A61B 17/04* (2006.01)
*A61B 17/062* (2006.01)
*A61B 17/06* (2006.01)

(52) U.S. Cl.
CPC ......... *A61B 17/0469* (2013.01); *A61B 17/0482* (2013.01); *A61B 17/0625* (2013.01); *A61B 2017/047* (2013.01); *A61B 2017/0472* (2013.01); *A61B 2017/06095* (2013.01)

(58) Field of Classification Search
CPC ........... A61B 17/0469; A61B 17/0482; A61B 17/0625; A61B 2017/047; A61B 2017/06095
USPC ................................. 606/144, 148
See application file for complete search history.

(56) References Cited

U.S. PATENT DOCUMENTS

| | | | |
|---|---|---|---|
| 5,084,058 A | 1/1992 | Li | |
| 5,324,298 A | 6/1994 | Phillips et al. | |
| 5,364,408 A * | 11/1994 | Gordon | 606/144 |
| 5,458,609 A | 10/1995 | Gordon et al. | |
| 5,496,348 A | 3/1996 | Bonnuti | |
| 5,562,684 A | 10/1996 | Kammerer | |
| 5,643,292 A | 7/1997 | Hart | |

(Continued)

FOREIGN PATENT DOCUMENTS

| | | |
|---|---|---|
| DE | 102005006705 | 8/2006 |
| WO | 2005/112789 | 12/2005 |

(Continued)

OTHER PUBLICATIONS

PCT International Search Report for International Application No. PCT/US2007/022240, mailed Mar. 28, 2008 (3 pp.).

(Continued)

*Primary Examiner* — Alexander Orkin
(74) *Attorney, Agent, or Firm* — Holland & Hart (57) ABSTRACT

A suture delivery device for insertion into an internal tissue wall opening and delivery of a suturing apparatus to the internal tissue wall is provided. In one embodiment, the suture delivery device comprises at least one carrier tube, at least one leg, and a tensioning device. The at least one carrier tube is configured to house a pusher and a suturing apparatus, the carrier tube having an expulsion end. The at least one leg is coupled to the at least one tube at a first end of the leg. The tensioning device is pivotally coupled to the at least one leg at a second end of the leg. When the at least one leg is in an open position, the tensioning device exerts tension on the leg such that the leg is movably suspended and can pivot about the tensioning device in response to contacting a tissue wall, and the pusher and suturing apparatus are in an delivery configuration for delivery of the suturing apparatus to the internal tissue wall.

19 Claims, 8 Drawing Sheets

(56) References Cited

U.S. PATENT DOCUMENTS

| | | | |
|---|---|---|---|
| 5,797,928 | A | 8/1998 | Kogasaka |
| 5,845,645 | A | 12/1998 | Bonutti |
| 5,868,762 | A | 2/1999 | Cragg et al. |
| 5,984,933 | A | 11/1999 | Yoon |
| 5,993,459 | A | 11/1999 | Larsen et al. |
| 6,059,800 | A | 5/2000 | Hart et al. |
| 6,074,395 | A | 6/2000 | Trott et al. |
| 6,132,439 | A | 10/2000 | Kontos |
| 6,283,947 | B1 * | 9/2001 | Mirzaee .................... 604/264 |
| 6,358,259 | B1 | 3/2002 | Swain et al. |
| 6,533,795 | B1 | 3/2003 | Tran et al. |
| 6,551,331 | B2 * | 4/2003 | Nobles et al. ............. 606/144 |
| 6,702,825 | B2 * | 3/2004 | Frazier et al. ............ 606/139 |
| 6,716,224 | B2 | 4/2004 | Singhatat |
| 6,855,124 | B1 * | 2/2005 | Gonzalez et al. ......... 604/96.01 |
| 6,896,685 | B1 * | 5/2005 | Davenport ................. 606/144 |
| 7,160,309 | B2 * | 1/2007 | Voss .......................... 606/144 |
| 7,226,467 | B2 * | 6/2007 | Lucatero et al. .......... 606/213 |
| 8,834,493 | B2 * | 9/2014 | Boehlke et al. ........... 606/144 |
| 2003/0040712 | A1 * | 2/2003 | Ray et al. ................... 604/173 |
| 2003/0181926 | A1 | 9/2003 | Dana et al. |
| 2003/0233107 | A1 * | 12/2003 | Gellman et al. ........... 606/144 |
| 2003/0233108 | A1 * | 12/2003 | Gellman et al. ........... 606/144 |
| 2004/0068273 | A1 * | 4/2004 | Fariss et al. ............... 606/144 |
| 2004/0097973 | A1 | 5/2004 | Loshakove et al. |
| 2005/0159812 | A1 | 7/2005 | Dinger et al. |
| 2006/0030868 | A1 | 2/2006 | Bennett |
| 2007/0203507 | A1 | 8/2007 | McLaughlin et al. |
| 2008/0033459 | A1 * | 2/2008 | Shafi et al. ................. 606/144 |
| 2008/0097479 | A1 | 4/2008 | Boehlke et al. |
| 2008/0097481 | A1 | 4/2008 | Schorr et al. |
| 2008/0097484 | A1 | 4/2008 | Lim et al. |
| 2008/0097527 | A1 | 4/2008 | Lim et al. |

FOREIGN PATENT DOCUMENTS

| | | |
|---|---|---|
| WO | 2007/067641 | 6/2007 |
| WO | 2007/116997 | 10/2007 |

OTHER PUBLICATIONS

English Abstract and Machine Translation of DE102005006705, Aug. 24, 2006.

* cited by examiner

INTERNAL SUTURING DEVICE LEG SUSPENSION SYSTEM AND METHOD OF USE

FIELD OF THE INVENTION

The present invention generally relates to medical systems and devices for suturing internal tissue walls, and more particularly to flexible needle and suture delivery units and devices.

BACKGROUND OF THE INVENTION

Various medical procedures, particularly cardiology procedures, involve accessing a corporeal vessel through the formation of a hole or opening in the vessel wall so that a medical procedure can be performed. After the particular medical procedure has been performed, the access hole in the vessel wall must be closed.

A number of prior vascular closure devices and methods have been developed in an attempt to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. No. 5,643,292 and U.S. Pat. No. 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use. Furthermore, many suturing devices dilate the vessel opening and perform the medical procedure via the vessel opening before the suture is extended across the vessel opening for approximation tissue surrounding the vessel wall.

Closure of vessel walls can result in trauma to the walls due to the insertion of rigid parts of a closure device into the vessel area to be closed. In order to lessen the amount of trauma to vessel walls when undergoing suturing procedures, there is a need for a closure device that may be configured to conform to surfaces having less elasticity compared to the suturing device.

BRIEF SUMMARY OF THE INVENTION

Flexible needle and suture delivery units and devices for delivering devices such as needles and sutures to internal tissue for closing internal tissue walls after an opening or puncture in tissue has been made are provided.

A suture delivery device for insertion into an internal tissue wall opening and delivery of a suturing apparatus to the internal tissue wall is provided. In one embodiment, the suture delivery device comprises at least one carrier tube, at least one leg, and a tensioning device. The at least one carrier tube is configured to house a pusher and a suturing apparatus, the carrier tube having an expulsion end. The at least one leg is coupled to the at least one tube at a first end of the leg. The tensioning device is pivotally coupled to the at least one leg at a second end of the leg. When the at least one leg is in an open position, the tensioning device exerts tension on the leg such that the leg is movably suspended and can pivot about the tensioning device in response to contacting a tissue wall, and the pusher and suturing apparatus are in an delivery configuration for delivery of the suturing apparatus to the internal tissue wall.

A suture system leg suspension device is further provided. In one embodiment, the suture system leg suspension device comprises at least one leg, at least one carrier tube, and a control device. The at least one leg and the at least one carrier tube each have an open position and a closed position. The at least one carrier tube is coupled to the at least one leg. The control device is operatively coupled to the at least one leg. The control device is configured to control actuation of the at least one leg from the closed position to the open position, thereby moving the carrier tube from the open position to the closed position. When the at least one leg is in an open position, the control device and leg form a leg suspension system having an elasticity for enabling the leg to move upon contacting a surface having a lesser elasticity than the elasticity of the leg suspension system.

Other features and advantages of the invention will become apparent from the following detailed description, taken in conjunction with the accompanying drawings which illustrate, by way of example, various features of embodiments of the invention.

DETAILED DESCRIPTION OF THE INVENTION

An needle and suture delivery unit and method for performing medical procedures that include delivering devices to internal tissue. In one embodiment, the needle and suture delivery unit may be used to deliver needles and sutures to internal tissue for closing internal tissue walls after an opening or puncture in tissue has been made is provided. Tissue that may be closed in accordance with the teachings herein may be part of a lumen such as a blood vessel, body cavity, other organ, or any tissue suitable for suturing. In one example, vascular suture delivery systems such as disclosed in copending U.S. patent application Ser. No. 11/551,523, filed Oct. 20, 2006 may be used to deliver needles and sutures for closing internal tissue walls after a medical procedure is performed through a vascular wall opening.

Figure 1A:
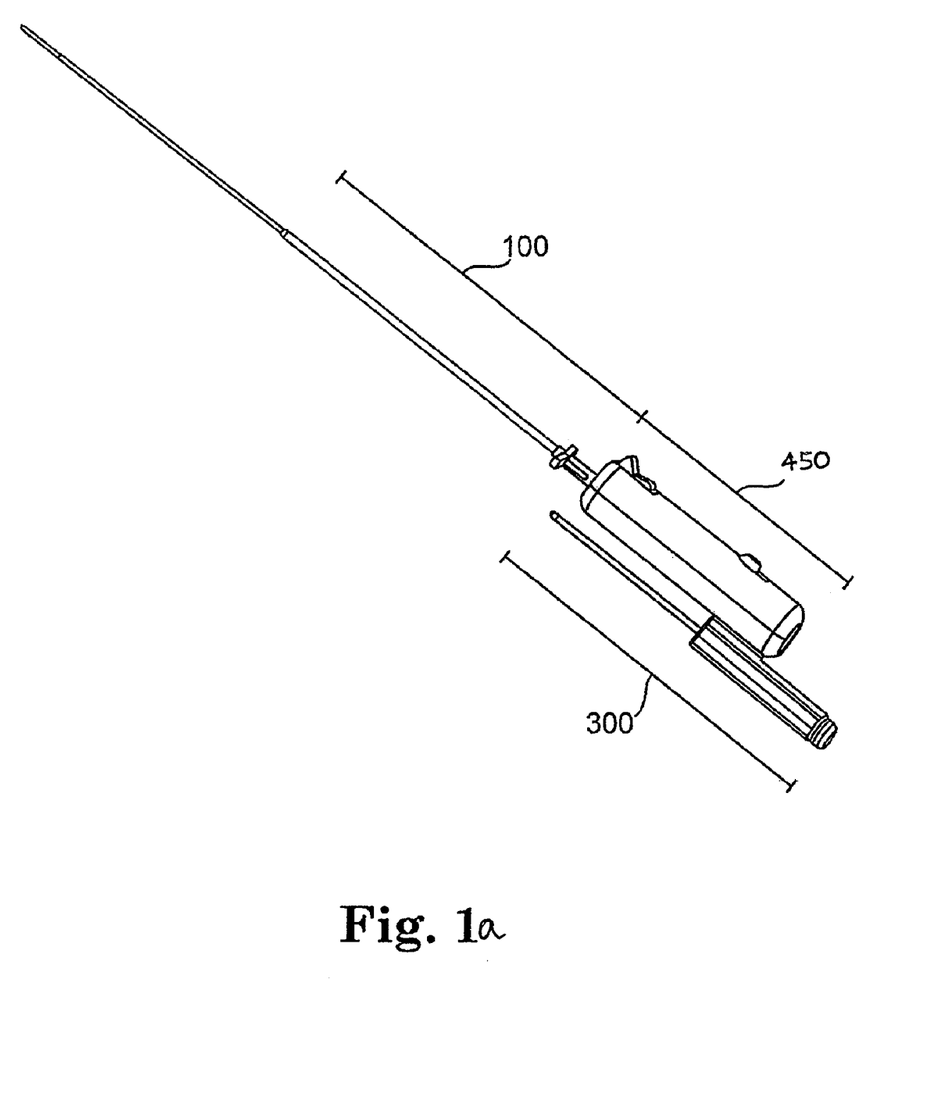
FIG. 1a illustrates a vascular suture delivery system including a needle and suture delivery unit in accordance with one embodiment.

Vascular suture delivery systems capable of delivering needles and sutures to the tissue are furnished with a needle and suture delivery unit which includes one or more pushers, needles, sutures, and legs, and is disposed at a distal end of a delivery unit. In alternative embodiments, the needle and suture delivery unit may be modified for delivering other devices to interior tissue of a body. In the embodiment of a needle and suture delivery unit, the needles and sutures may be delivered to the intima of an artery such as the femoral artery. The needle and suture delivery unit is insertable into tissue, such as the artery, so that one or more needles and sutures may be delivered to the internal tissue of the patient. As shown in FIG. 1a, the vascular suture delivery system comprises a handle 450, a needle and suture delivery unit 100, and a suture knot system 300. As will be described more fully below, the handle includes a control unit for controlling the needle and suture delivery unit. A tube or sheath may be provided and may serve as a cover for all or a portion of the needle and suture delivery unit. The sheath may be pulled back or peeled away to expose the distal end of the needle and suture delivery unit.

Figure 1B:
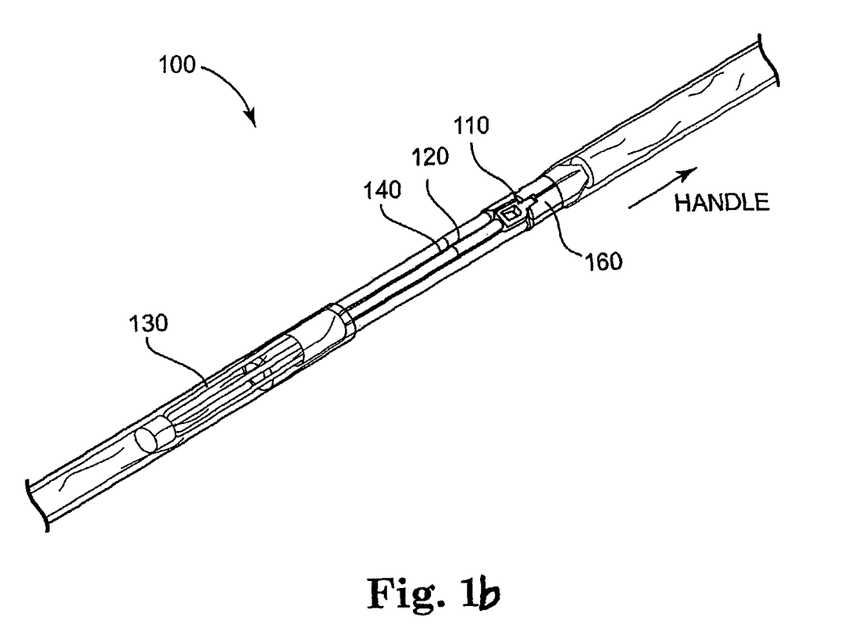
FIG. 1b illustrates a suture and delivery unit of a vascular suture delivery system, the suture and delivery unit including four sets of legs, needle carrier tubes, pushers, needles, and sutures, where the legs are in a closed position.
Figure 2A:
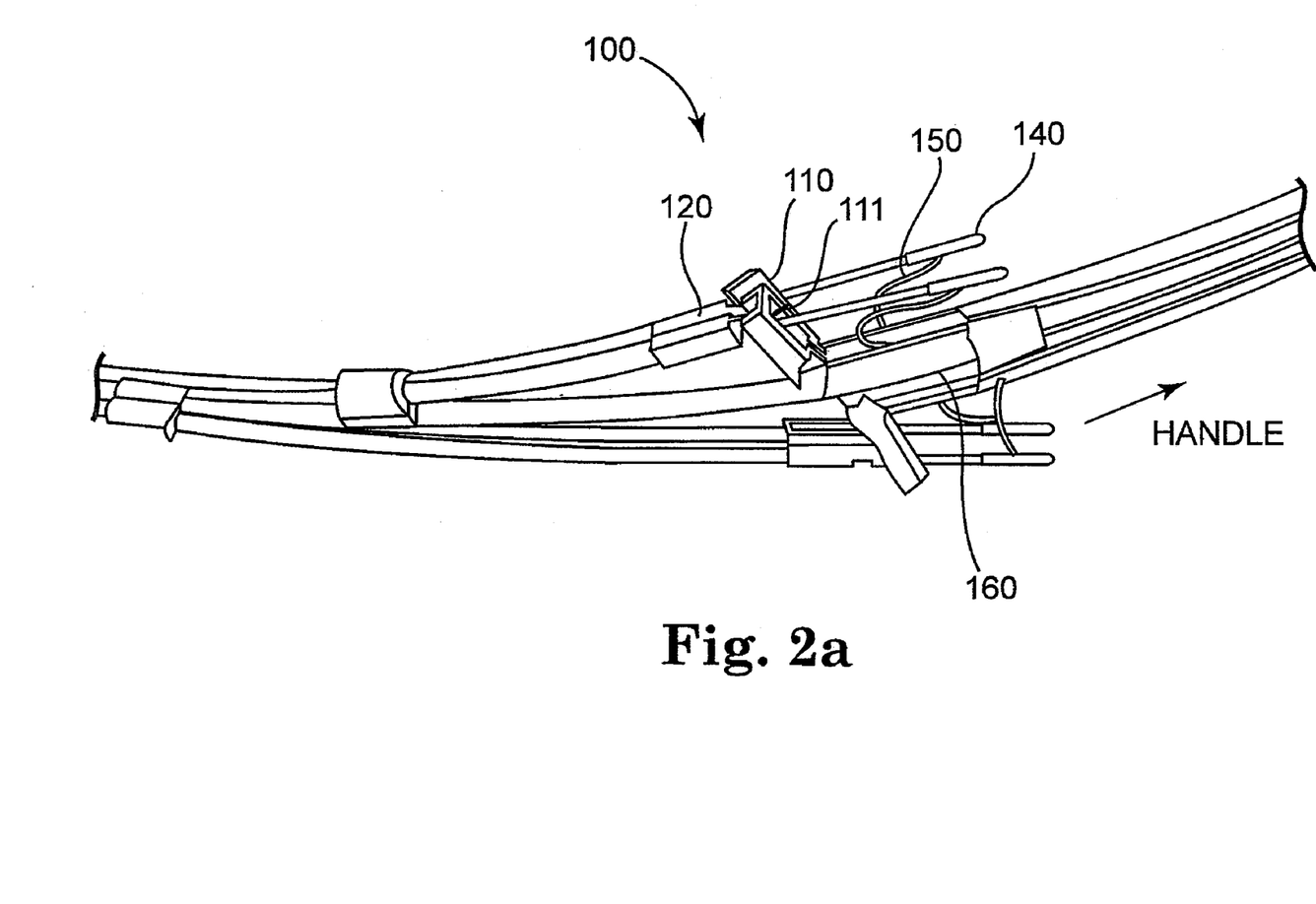
FIGS. 2a and 2b illustrate a suture and delivery unit having four sets of legs in an open position, pushers, needles, and sutures in accordance with one embodiment.
Figure 2B:
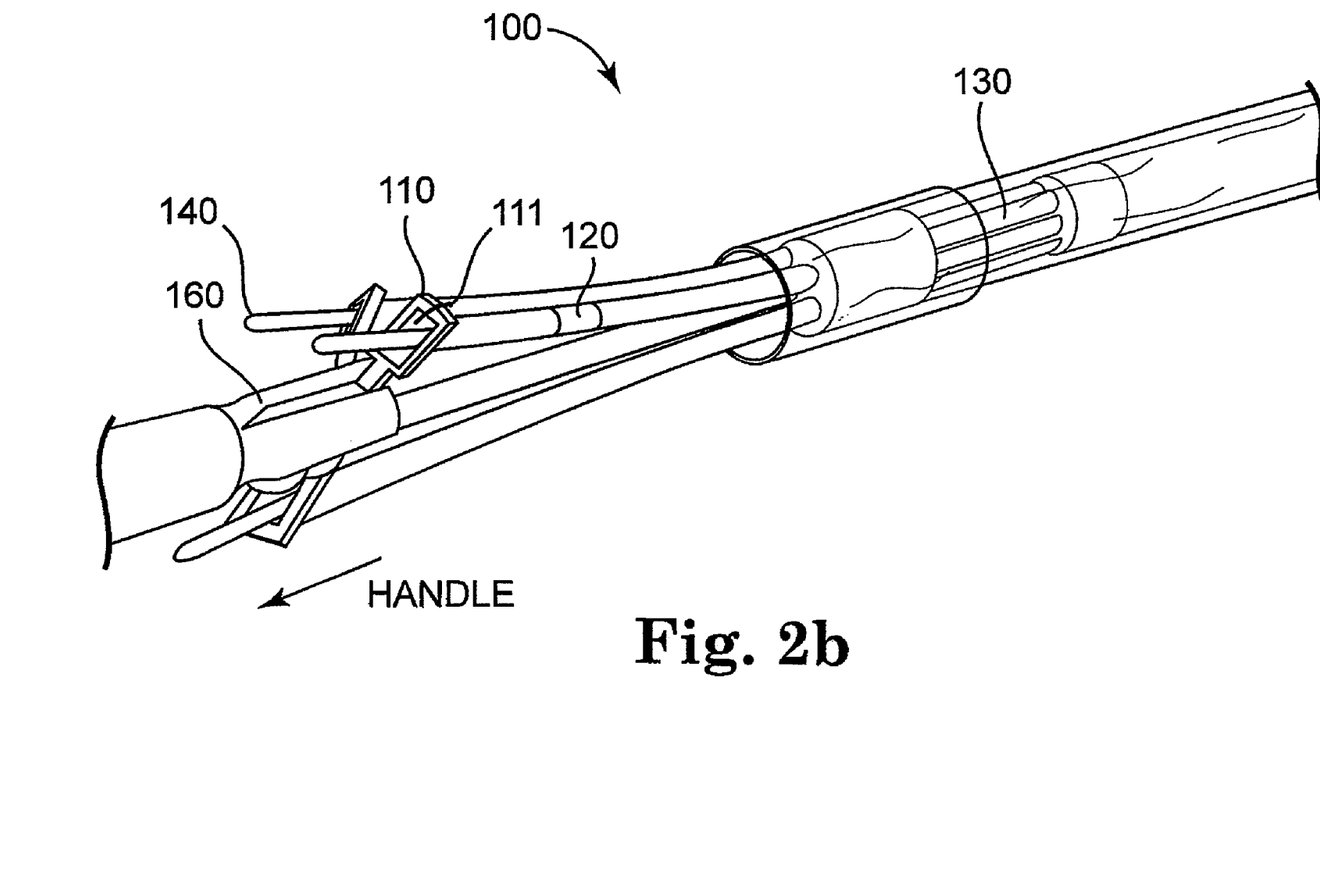

FIGS. 1b, 2a, and 2b depict a first embodiment of needle and suture delivery unit 100 of the vascular suture delivery system. FIG. 1b shows the needle and suture delivery unit 100 in a closed position and FIGS. 2a and 2b show the needle and suture delivery unit 100 in an open position. FIG. 1b illustrates the suture delivery unit 100 including legs 110, needle carrier tubes 120, pushers 130, needles 140, and a support 160. FIG. 2a illustrates the suture delivery unit 100 including legs 110, openings 111 in the interior of the legs 110, needle carrier tubes 120, needles 140, sutures 150, and the support 160. FIG. 2b illustrates the suture delivery unit 100 including legs 110, openings 111, needle carrier tubes 120, pushers 130, needles 140, and support 160. In the embodiments shown, the needle and suture delivery unit 100 comprises four sets of legs 110, needle carrier tubes 120, pushers 130, needles 140, and sutures 150, where the legs 110 are in a closed position. It is to be noted that in alternative embodiments, more or fewer sets of legs, needle carrier tubes, pushers, needles, and sutures may be used. Further, the number of legs, needle carrier tubes, pushers, needles, and sutures may not be equal. Reference may be made to proximal and distal positions or movements. For the purposes of description, proximal generally refers to towards the handle of the vascular suture delivery system or towards the surgeon and distal generally refers to towards the patient. It is to be noted that, in some embodiments, the relative orientation of components of the vascular suture delivery system may be altered.

Figure 3:
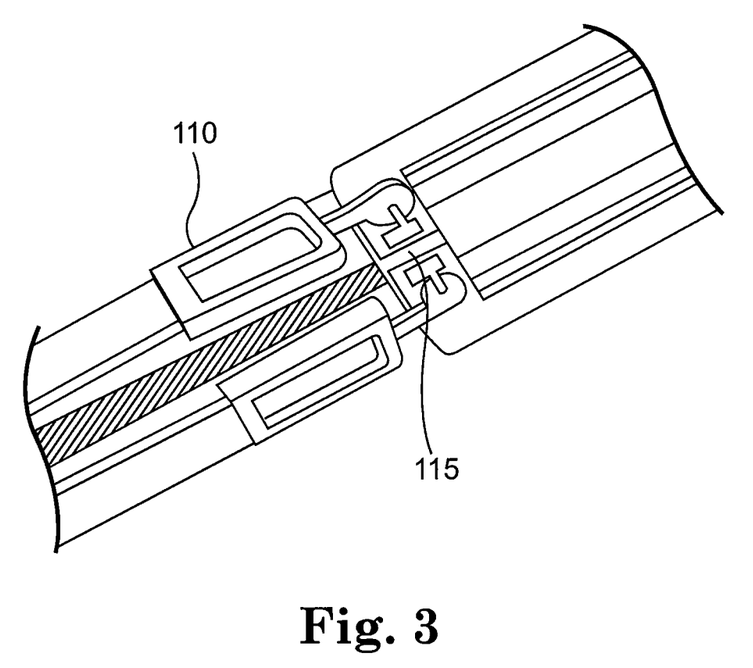
FIG. 3 illustrates a tensioning cable coupled to legs of the suture and delivery unit in accordance with one embodiment.

Referring again to the figures, for purposes of description, one set of the legs 110, needle carrier tubes 120, pushers 130, needles 140, and sutures 150 is described. In this configuration, the needle and suture delivery unit 100 is insertable into a vessel wall, and the leg 110, needle carrier tube 120, pusher 130, and needle 140 are aligned parallel to a support 160. As can be seen in FIG. 1b, the needle carrier tube 120 is coupled to the leg 110. More specifically, in the embodiment shown, the tube 120 is hinged to the leg 110. The support 160 supports the leg 110, which in turn supports the tube 120. In the closed configuration, shown in FIG. 1b, both the tube 120 and the leg 110 are aligned generally parallel to the support 160. FIG. 3 illustrates a tensioning cable coupled to legs of the suture and delivery unit. In an area proximal to the support 160, the leg 110 is also coupled to a cable 115, shown in FIG. 3, which serves to actuate the leg 110 from a closed position to an open position, and vice versa.

Pushers 130 and needles 140 of the needle and suture delivery unit 100 may be slidably disposed within the needle carrier tube 120. The needle carrier tube 120 may have any suitable cross section such as a circular cross section or a square cross section. The needle carrier tube 120 has a needle expulsion end from which the needle 140 is expelled to deploy the needle 140 and suture 150. The needle expulsion end may be the distal end of the needle or the proximal end of the needle in various embodiments. In the embodiments shown, the needle expulsion end of the needle carrier tube 120 is the proximal end of the needle carrier tube 120. The pusher 130 likewise has a needle engagement end. The needle engagement end of the pusher 130 is the end of the pusher 130 that engages the needle 140 to expel the needle 140 from the needle carrier tube 120. The pusher 130 may be grounded and/or the needle engagement end of the pusher 130 may have adaptive features to enable coupling with the needle, described more fully below. The needle engagement end of the pusher 130 may be the proximal end of the pusher or the distal end of the pusher in various embodiments. In the embodiments shown, the needle engagement end of the pusher 130 is the proximal end of the pusher 130. Thus, the needle engagement end of the pusher 130 engages the needle 140 to expel the needle 140 from the needle expulsion end of the needle carrier tube 120. More specifically, in the embodiments shown, the proximal end of the pusher 130 engages the needle 140 to expel the needle 140 proximally from the proximal end of the needle carrier tube 120.

The needle 140 may be constructed of implantable stainless steel, a dissolvable polymer, or other material suitable for engaging with tissue. The needle 140 includes a sharp end and an opposite end whose face is approximately perpendicular to a central axis of the needle. In alternative embodiments, the opposite end to the sharp end my have different configurations.

As discussed, the pusher 130 acts to expel the needle 140 from the carrier tube 120. In one embodiment, the needle 140 is positioned in the carrier tube 120 such that the sharp end of the needle 140 is oriented toward the needle expulsion end of the carrier tube 120 and the opposite end of the needle 140 is oriented toward the needle engagement end of the pusher 130. In this embodiment, the needle 140 is delivered from the needle carrier tube 120 sharp end-first. Generally, the needle 140 engages with tissue after it is fully delivered from the tube 120. Once the needle 140 engages with tissue, such as by embedding in tissue, it is substantially prevented from re-entering the tube 120.

In alternative embodiments, the delivery system may be used to deliver suturing apparatuses other than needles. For example, the delivery system may be used to deliver a pronged projectile or other suitably shaped projectile for engaging with tissue.

The pusher 130 may have any suitable configuration. As previously discussed, the needle engagement end of the pusher 130 may have adaptive features to enable the needle engagement end of the pusher 130 to engage the needle 140 or to couple with the needle 140. In the embodiments shown, the pusher 130 comprises a rod-like structure wherein the needle engagement end of the pusher 130 is configured to be received by the opposite end of the needle 140 such that the needle 140 is carried by the pusher 130. The pusher 130 is configured for movement towards the expulsion end of the needle carrier tube 120. In one embodiment, such movement is in response to a springing action exerted on the pusher 130, either directly or via an actuating member. As discussed more fully in copending U.S. patent application Ser. No. 11/551,523, filed Oct. 20, 2006; and Ser. No. 11/551,620, filed Oct. 20, 2006, entitled "Method and Device for Automated Needle Deployment", herein incorporated by reference, the springing action may result from actuating a flywheel (see 420 of FIG. 5b) associated with the delivery unit handle. With use of a flywheel, after movement toward the needle engagement end of the needle carrier tube 120, the pusher 130 reenters the needle carrier tube 120 as the flywheel rotation continues. In alternative embodiments, the pusher 130 may be compelled for movement towards the needle expulsion end of the needle carrier tube 120 using other mechanisms. Similarly, a separate mechanism may be used to retract the pusher 130 into the needle carrier tube 120. In some embodiments, the needle and suture delivery unit may be oriented such that the pusher 130 moves distally to push the needle 140 from the carrier tube 120 distally. The combination of the length of the pusher 130 and the distance the pusher 130 moves may result in the needle engagement end of the pusher 130 moving through and out of the needle carrier tube 120. The pusher 130 may substantially exit the needle carrier tube 120 to expel the needle 140, may partially exit the needle carrier tube 120, or may not exit the needle carrier tube 120.

The suture 150 of the needle and suture delivery unit 100 may be composed of a variety of materials such as nylon, a dissolvable polymer, metal, or any suitable resorbable or nonresorbable suture material. The suture 150 may be braided. One or more sutures may be disposed on each needle 150 or other projectile of the needle and suture delivery unit 100. Thus, at least one end of the suture 150 is coupled to a needle 140. Initially, the length of the suture is of a length such that the suture 150 extends from the needle 140 as engaged with the tissue, out of the tissue of the patient, and toward the delivery unit handle. A portion of the suture 150 may be disposed in the tube 120, trailing from the needle 140, before the needle 140 is delivered to tissue.

The leg 110 of the needle and suture delivery unit 100 serves as a guide for the tube 120, the pusher 130, and the needle 140 that may be deployed from the tube 120. More specifically, the leg 110 moves the tube 120 from the closed configuration shown in FIG. 1b to the open configuration shown in FIGS. 2a and 2b such that the pusher 130 may expel the needle 140 from the tube. More specifically, in the open configuration, the legs form a temporary anchoring and firing base for the needles 140 provided in the needle carrier tubes 120. The leg 110 may be constructed of stainless steel, a polymer, or any material suitable for medical devices. A leg may be coupled at one end to the support 160 and one or more tensioning cables 115, and optionally may be coupled at another end to a needle carrier tube 120. The leg 110 may further comprise a passage or aperture through a central region and may be used as a guide or support for other portions of the needle and suture delivery unit 100. The leg 110 is movable from a closed position, shown in FIG. 1b, which is parallel to the support 160, to an open position, shown in FIGS. 2a and 2b, in which the leg 110 is disposed at an angle relative the support 160. That angle may range from approximately 30° to approximately 70° or from approximately 30° to approximately 90°.

In the closed position, the needle carrier tube 120 may generally abut a first end of the leg 110 and be hinged to that end of the leg 110. Alternatively, in the closed position, the needle carrier tube 120 may overlap a portion of the leg 110. Thus, a portion of the needle carrier tube 120 may lie within the leg 110. Generally, the needle carrier tube 120 and the leg 110 lie parallel to the support 160 and do not protrude beyond the surface of the support 160. In the closed position, the needle and suture delivery unit 100 is configured to be insertable into the tissue of the patient, for example into the intima of an artery, and may be enclosed by a sheath so as to avoid subjecting the tissue to unnecessary trauma.

In the open position, needle carrier tube 120 pivots about the leg 110, for example via a hinge connection of the needle carrier tube 120 to the leg 110, such that the leg is disposed at an angle to the support 160. In alternative embodiments, in the open position, the leg 110 is at an angle between parallel and perpendicular to the support 160, such as between approximately 30° and approximately 70°. In the open position, the leg 110 moves the needle expulsion end of the needle carrier tube 120 from the support 160, the needle carrier tube 120, pivoting at its coupling to the leg 110 such that it is disposed at an angle to the leg 110. For example, in one embodiment, in the open position, the needle carrier tube 120 is approximately perpendicular to the leg 110. In the open position, the leg 110 serves as a brace for the needle carrier tube 120, but may also be pliable and adaptable to the contours of the vessel. Further, when the leg 110 in the open position, the pusher 130 and needle 140 are positioned for deployment.

A tensioning cable 115, shown in FIG. 3, may be provided coupled to each leg 110 and extending towards the handle or other control mechanism of the delivery device. A single tensioning cable 115 may be provided for coupling to one or more legs 110 or a tensioning cable 115 may be provided for each leg 110. At or near the control mechanism of the handle, the tensioning cable 115 terminates to a tensioning device such as a spring. In alternative embodiments, a tensioning device provided between the leg 110 and the control mechanism may include a wire cable having elastic properties or other suitable material that is configured to stretch when under tension. Regardless of the type of tensioning mechanism used, whether a tensioning cable 115 or other tensioning device, the tensioning mechanism serves to actuate the legs 110 from a closed position to an open position, or vice versa. When the leg 110 is in a closed position, the tensioning mechanism is relaxed. When the leg 110 is in an open position, the tensioning mechanism is in tension. The tension exerted on the leg 110 allows it to open to at or near its maximum position, and to flex when contacting a less elastic, nonconforming surface. The tension exerted on the leg 110 slaves the leg 110 in a manner that causes the leg 110 to be pliable so that it moves when contacting more rigid surfaces having a higher tension than the tension exerted on the leg 110. This may allow the needle and suture delivery unit 100, and more specifically, the legs 110 of the needle and suture delivery unit 100 to conform to the interior of the vessel or lumen of interest.

When the leg 110 is in an open position, the needle carrier tube 120 pivots with respect to the leg 110 such that the needle carrier tube 120 is disposed at an angle to the leg 110. In one embodiment, in an open position, the needle carrier tube 120 may be approximately perpendicular to the leg 110 In some embodiments, the needle carrier tube 120 may be coupled to the leg 110 by a male/female connection; in other embodiments, the needle carrier tube 120 may rest inside an opening 111 (see FIG. 2a) which extends through an interior region of leg 110, or the needle carrier tube 120 can pass through the opening 111 and extend slightly beyond leg 110 (see FIG. 2b). The opening 111 enables the pusher 130 and needle 140 to be slidably disposed in the needle carrier tube 120 to be guided through the leg 110 when in an open position. FIG. 2b depicts the needle and suture delivery unit 100 with the needle engagement end of the pusher 130 extending through and beyond the leg 110. In this embodiment, a needle 140 present in the needle carrier tube 120 before deployment of the pusher 130 expelled from the needle carrier tube 120 and into tissue as the needle engagement end of pusher 130 reaches its extended position.

In the illustrations of FIGS. 2a and 2b, the leg 110 is in an open position. Thus, the cable 115 is in a tensed state and the leg 110 is capable of pivoting and flexing about its connection point(s), thus providing leg 110 with a flexibility that allows the needle and suture delivery unit and needle delivery unit to conform to the intima of the vessel, artery, or vein of interest thereby minimizing intima trauma). In the embodiment shown, the needle engagement end of the needle carrier tube 120 is the proximal end of the needle carrier tube 120. Thus, the connection point of the cable 115 to the leg 100 is at a proximal end of tube 120 (FIG. 2a) and/or at a distal end of support 160 (FIGS. 2a and 2b). When the leg 110 is connected only to the support 160 (FIG. 2b), increased flexibility may be provided because it pivots about a single pivot point. Further, flexibility may alternatively be provided by coupling the tube 120 to the leg 110 via the opening 111 in a variety of positions (e.g., FIG. 2Aa), rather than via a connection point (FIG. 2b).

It should be understood that any number of legs, pushers, needles, and sutures may be used in needle and suture delivery units of the present invention. In the figures, two and four sets of legs, pushers, needles, and sutures are depicted.

Figure 4:
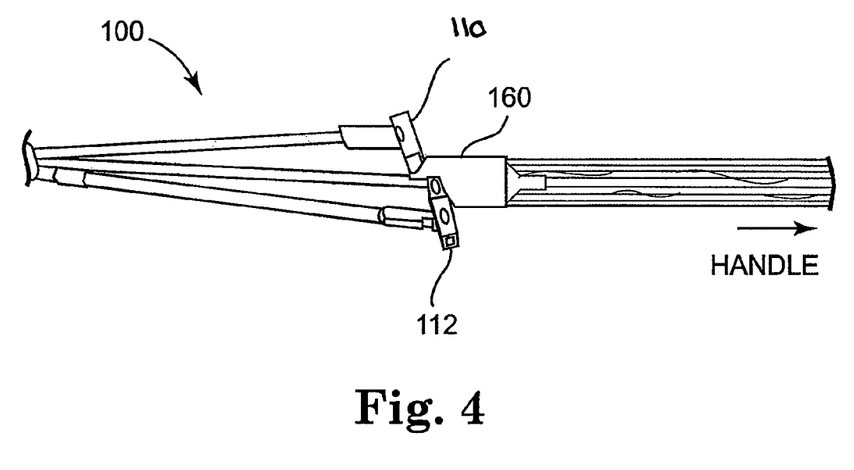
FIG. 4 illustrates a suture and delivery unit in accordance with a further embodiment.

FIG. 4 illustrates a further embodiment of the needle and suture delivery unit 100. The needle and suture delivery unit 100 includes front legs 110 and back legs 112. The front legs 110 are positioned closer to the distal end of the needle delivery unit, and the back legs 112 are positioned closer to the proximal end of the needle delivery unit and handle or control mechanism. Both the front legs 110 and the back legs 112 may be substantially configured and operated as discussed with respect to the legs 110 of FIGS. 1b, 2a, and 2b. In the open position, the front legs 110 and the back legs 112 are disposed at angles to the support 160. In one embodiment, the front legs 110 are disposed approximately 70° from the support 160 and the back legs 112 are disposed approximately 30° from the support 160. The front legs and the back legs 110, 112 may be of the same configuration or may be of differing configurations. In the example of FIG. 4, the configurations of the front legs and the back legs 110, 112 are substantially the same with the positioning of the front legs and the back legs 110, 112 on the support 160 resulting in their categorization as front and back.

Each leg 110, 112 is operatively coupled to a tensioning mechanism such as a cable or wire rope extending to the handle; a first cable may be operatively coupled to the front leg(s) 110, and a second cable may be operatively coupled to the back leg(s) 112. Alternatively, a cable may be provided for each leg or all of the legs 110, 112 may be coupled to a single cable. Both the first and second cables may be substantially configured and operated as discussed with respect to the tensioning cable 115 of FIG. 3 FIGS. 1b, 2a, and 2b. In some embodiments, the flexibility of the cables may vary one to the other. For example, a more flexible cable may be coupled to the back leg 112 so that when back leg 112 is suspended in the open position, it has more flexibility compared to front leg 110 coupled to a less flexible cable. The flexibility of legs 110, 112 may also be varied by adjusting spring forces when the first and second cables are coupled to springs.

Figure 5A:
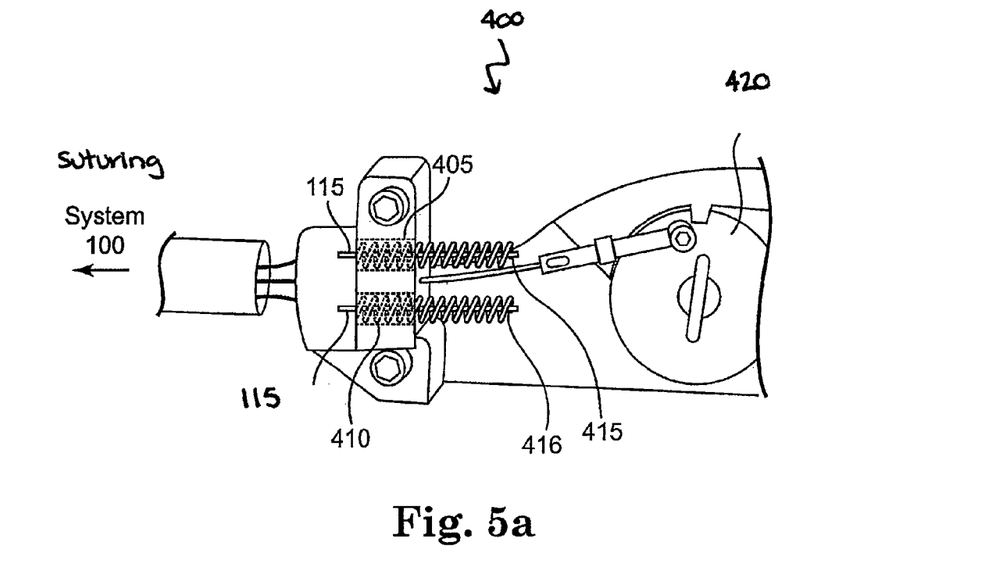
FIGS. 5a and 5b illustrate a handle of the vascular suture delivery system, the handle including a control unit for controlling operations of the suture and delivery unit in accordance with one embodiment.
Figure 5B:
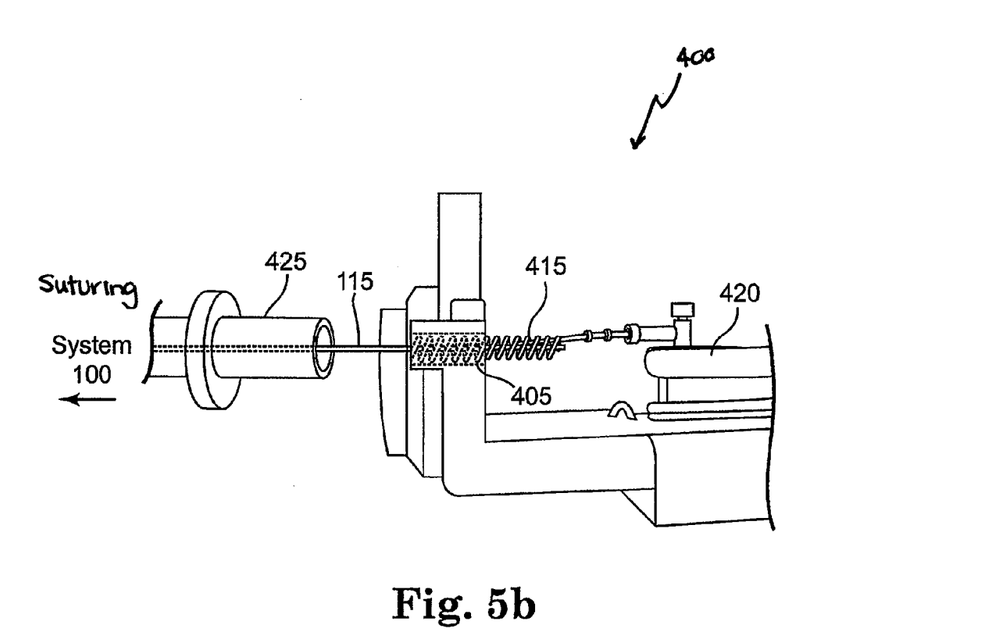

FIGS. 5a and 5b show a control unit 400 of the handle of the vascular closure delivery device. As shown, the control unit 400 may include springs 415, 416 positioned in respective channels 405, 406, tensioning cables 115 extending from the springs 415, 416 and into a sheath 425, and a flywheel 420 for deploying portions of the suturing system. The control unit 400 controls operations of the needle and suture delivery unit 100. The control unit 400 may be located at, on, or proximate the handle of the vascular closure delivery device. FIG. 5a illustrates a top view of the control unit 400 and springs 415 and 416 coupled to the tensioning cables 115 of FIG. 4. Each of the springs 415, 416 extend both exterior to and through channels 405, 410, respectively. In alternative embodiments, springs or other mechanisms and associated channels may have a variety of configurations. Generally, any suitable spring or tensioning mechanism may be used. Spring forces of springs 415, 416 can be adjusted so that the degree of flexibility of the legs 110, 112 may be controlled or adjusted. For example, lighter springs or stronger springs (varying elastic forces) may be used to alter the leg flexibility. Leg flexibility can also be controlled by varying the length of spring channels 405, 410 that house at least a portion of springs 415, 416. The front legs and the back legs 110, 112 may further be configured to have a differing amount of flexibility depending on application. For example, a weaker spring can be used for the back legs to get more flexibility compared to the front legs. In addition, multiple springs, rather than a single spring may be used to control the flexibility of each leg. The above-described features may also be provided by using highly elastic cables that stretch when under tension or using other mechanisms.

FIG. 5b illustrates a side view of the control unit 400 having a tensioning device composed of cables and springs. The tensioning cable 115 is shown extending from the spring 415, through the channel 405, and into sheath 425 where it couples with a leg 110 of the needle and suture delivery unit 100. In the embodiments shown, the needle carrier tube 120 is oriented for expulsion of the needle 140 proximally. Thus, the leg 110 may be moved to the opened configuration by exerting a pull force on the leg 110 and drawing the end of the leg 110 coupled to the needle carrier tube 120 proximally. Thus, a lever or sliding platform may be provided for exerting a pull force on the leg 110. The tensioning cable(s) 115 may be coupled directly or indirectly to the lever or sliding platform. Once the legs 110, 112 open, the cables 115 are in a tensed state, and the legs 110, 112 are able to pivot about their connection points. Because the tensioning device is operatively coupled to legs 110, 112 via coupling of the cables 115, the legs 110, 112 are pliable when subjected to other forces. This increases the overall flexibility of the delivery unit resulting in a delivery unit that can yield to vessel walls or other portions of tissue that can be traumatized from insertion of rigid portions of a delivery unit. To return the needle and suture delivery unit to a closed configuration, the lever or sliding platform is returned to its original position.

FIGS. 5a and 5b further illustrate a flywheel 420 that may be used to deploy the pusher 130 to expel the needle 140 from the needle carrier tube 140, as previously discussed. The springs 415, 416 extending both exterior to and through channels 405, 410 form a tensioning mechanism allowing the legs to flex. Leg flexibility can also be controlled by varying the length of spring channels 405, 410 that house at least a portion of springs 415, 416. As discussed, a lever or sliding platform may exert a pull force on the legs to open the legs. When the platform is moved, for example proximally, to open the legs, the springs 415, 416 are in tension. The springs 415, 416 maintain the legs in an open position but permit the legs to flex.

Figure 6:
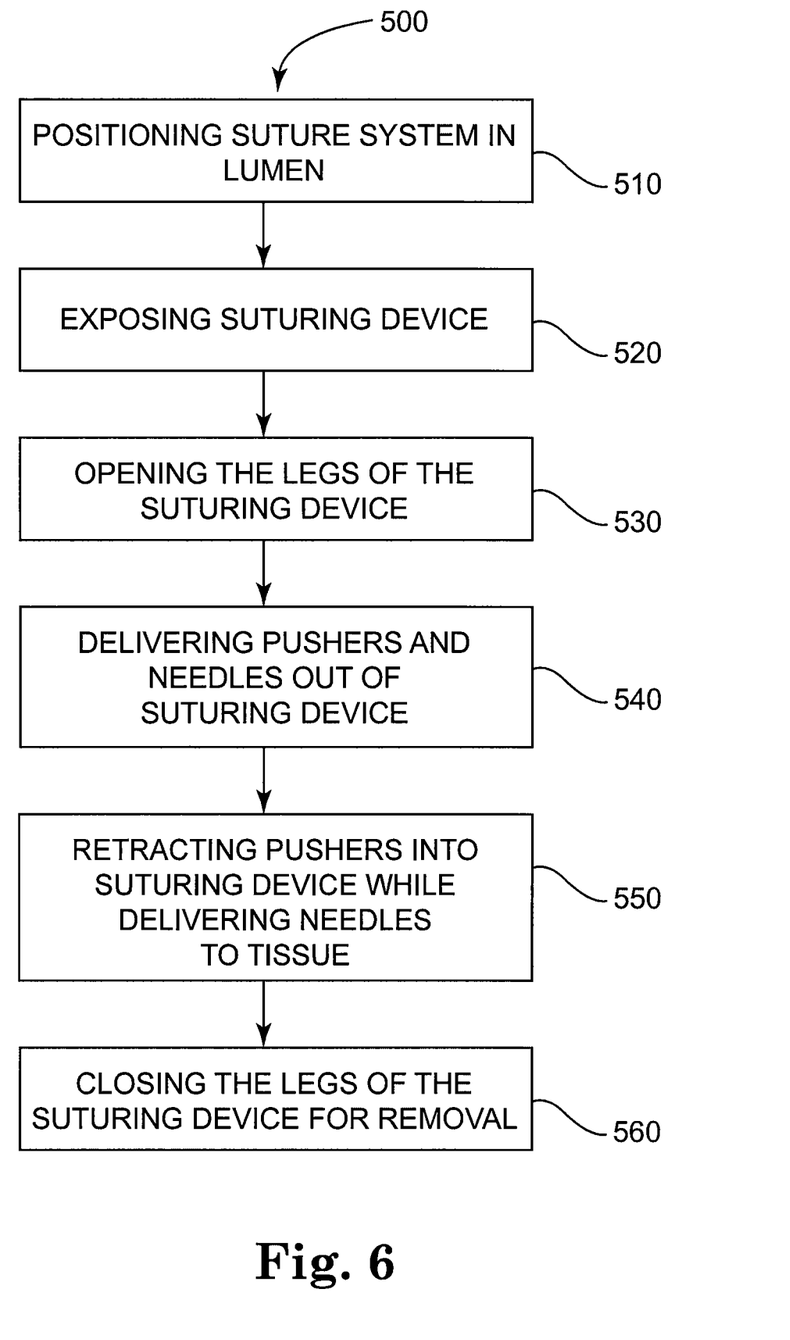
FIG. 6 illustrates a method of using the needle and suture delivery unit in accordance with one embodiment.

FIG. 6 depicts one embodiment of a method 500 of using the suture system. The method 500 involves positioning 510 the needle and suture delivery unit. In one embodiment, positioning 510 the needle and suture delivery unit comprises positioning the needle and suture delivery unit in a lumen using a locator. Using a standard locator, when blood no longer flows through the locator, the correct location has been established. After positioning 510 of the needle and suture delivery unit, a sheath is retracted to expose 520 the suturing device. The legs of the suturing device may then be opened 530. In one embodiment, the legs are moved to an open position by deploying a pull force on a lever of sliding platform disposed on the handle. The pull force pulls the legs to an open configuration via the tensioning cables. Movement of the legs in turn pulls the needle carrier tubes to the operational open position Tactile feedback may indicate to the user to stop applying pull force when the legs have opened. In the open position, the legs are disposed at an angle to the support, for example, generally perpendicular to the support, and are flexibly suspended via a tensioning device which may be located at the handle of the vascular suture delivery unit. The needles are expelled from the needle carrier tubes by, for example, deploying 540 the pushers, thereby deploying the needles. In one embodiment, such delivery is performed by releasing a push button actuator on the handle. Thus, for example, the push button may actuate a wire connected to a flywheel, and release of the flywheel may cause the pushers to spring forward through the tubes. Needles provided operatively associated with the needle engagement end of the pushers are thereby expelled from the needle carrier tubes. Continued movement of the flywheel causes the pushers to retract. As the pushers retract, the needles engage tissue 550. Engagement of the tissue prevents the needles from retracting with the pushers. After the suture system deploys the needles, the legs can be moved to a closed position 560, for example by returning the lever or sliding platform to its original position, such that the suture system assumes an insertion/removal configuration allowing the needle and suture delivery unit to be removed from the vessel.

The vascular suture delivery system and the needle and suture delivery unit have been particularly discussed in relation to delivering needles and sutures to close a vascular would or puncture. It is to be appreciated that the delivery system and delivery unit may be used to delivery other devices to tissue of the body. Thus, although the present invention has been described with reference to preferred embodiments, persons skilled in the art will recognize that changes may be made in form and detail without departing from the spirit and scope of the invention.

What is claimed is:

1. A suture delivery device for insertion into an internal tissue wall opening and delivery of a needle to the internal tissue wall, the suture delivery device comprising:
    a support;
    a needle carrier tube having a support end and a needle expulsion end, the needle expulsion end being at a proximal end of the needle carrier tube;
    a needle having a sharp end and an opposite end, the needle being slidably disposed within the needle carrier tube such that the needle may be expelled from the needle expulsion end of the needle carrier tube to deploy the needle and wherein the needle is configured such that, upon deployment from the needle carrier tube, the needle is substantially prevented from re-entering the needle carrier tube;
    a suture coupled to the needle wherein the suture is deployed with the needle;
    a pusher positioned distal to the needle in the needle carrier tube, the pusher being configured to move proximally provided for moving in the needle carrier tube to expel the needle from the needle expulsion end of the needle carrier tube to deliver the suture;
    a leg having a first end and a second end, the first end of the leg being coupled to the support end of the needle carrier tube, the second end of the leg being coupled to the support, wherein actuation of the leg actuates the suture delivery device between a closed position and an open position;
    a tensioning device, the tensioning device pivotally coupled to the leg at the second end of the leg, wherein the tensioning device is configured to actuate the leg to actuate the suture delivery device between the closed position and the open position, the support being stationary while the leg is actuated;
    wherein, in the closed position, the needle carrier tube and the leg are generally aligned with each other and are arranged generally parallel to the support and wherein, in the open position, the needle carrier tube is disposed at an angle to the leg such that the needle carrier tube and the leg are not aligned, and the leg is disposed at a non-parallel angle to the support.

2. The suture delivery device of claim 1, wherein the leg is hinged to the needle carrier tube such that the needle carrier tube is able to move independently from the leg.

3. The suture delivery device of claim 1, wherein, when the suture delivery device is in the closed position, the device is in an insertion configuration for insertion into the internal tissue wall opening.

4. The suture delivery device of claim 1, wherein the support is part of the tensioning device.

5. The suture delivery device of claim 1, wherein the leg is materially coupled to the tensioning device.

6. The suture delivery device of claim 1, wherein the leg is disposed at an angle between approximately 30 degrees and approximately 70 degrees to the support in the open position.

7. The suture delivery device of claim 1, wherein the leg is disposed at an angle between approximately 30 degrees and approximately 90 degrees to the support in the open position.

8. The suture delivery device of claim 1, wherein, in the closed position, the pusher is provided distally of the needle carrier tube.

9. The suture delivery device of claim 1, wherein, in the closed position, the pusher is provided at least partially in the needle carrier tube.

10. The suture delivery device of claim 1, wherein the needle expulsion end of the needle carrier tube is a proximal end and wherein the needle is expelled proximally from the needle carrier tube.

11. The suture delivery device of claim 1, wherein, when the suture delivery device is in the open position wherein, when the suture delivery device is in the open position, the tensioning device exerts tension on the leg such that the leg is movably suspended and can pivot about the tensioning device in response to contacting a tissue wall, and the pusher and needle are in a delivery configuration for delivery of the needle and suture to the internal tissue wall.

12. The suture delivery device of claim 1, further comprising a cable coupled at a distal end of the tensioning device and to the support end of the leg and an elastic device coupled to a proximal end of the cable.

13. A suture system leg suspension device comprising:
    a support;
    a leg coupled to the support;
    a carrier tube coupled to the leg, wherein actuation of the leg actuates the carrier tube between a closed position and an open position, and wherein, in the closed position the leg and the carrier tube are generally aligned with each other and with the support and, in the open position, the carrier tube is disposed at an angle to the leg and the support such that the carrier tube, the leg, and the support are not aligned;
    a needle slidably disposed within the carrier tube such that the needle may be expelled from the carrier tube when the carrier tube is in the open position and wherein the needle is configured such that, upon expulsion from the carrier tube, the needle is substantially prevented from re-entering the carrier tube;

a pusher positioned distal to the needle in the carrier tube, the pusher being configured to expel the needle from a proximal end of the carrier tube upon proximal movement of the pusher;

a control device operatively coupled to the leg, the control device being configured to control actuation of the leg, thereby moving the carrier tube from the open position to the closed position, the support being stationary while the leg is actuated;

wherein when the leg is in an open position, the control device and leg form a leg suspension system having an elasticity for enabling the leg to move upon contacting a surface having a lesser elasticity than the elasticity of the leg suspension system.

14. The suture system leg suspension device of claim 13, wherein the control device further comprises a cable coupled to the leg, wherein the cable extends from the leg to the control device, such that the leg is operatively coupled to the control device via the cable.

15. The suture system leg suspension device of claim 14, wherein the cable is configured to have an elastic force, and the leg coupled to the cable movable upon contacting a surface having a less elastic force than the elastic force of the cable.

16. The suture system leg suspension device of claim 13, comprising at least two legs, wherein one of the at least two legs comprises a front leg and another of the at least two legs comprises a back leg situated proximally to the control device compared to the front leg.

17. The suture system leg suspension device of claim 16, wherein the control device comprises at least two springs, wherein a first spring comprises a first elastic force and is operatively coupled to one of the at least two legs, and a second spring comprises a second elastic force different from the first spring and is operatively coupled to another of the at least two legs.

18. The suture system leg suspension device of claim 17, wherein the first and second springs provide flexibility to the at least two legs and wherein an elastic force of the first and second springs may be selected based on desired flexibility.

19. The suture system legs suspension device of claim 16, wherein the control device further comprises at least two springs having the same elastic force, each enclosed in a spring channel of the control device and operatively coupled to each of the at least two legs, wherein a first spring channel comprises a first length and a second channel comprises a second length different from the first length such that the tension on the legs is different due to the differing lengths of the spring channels.

* * * * *